United States Patent
Segura-Orsoni et al.

(10) Patent No.: US 8,815,938 B2
(45) Date of Patent: Aug. 26, 2014

(54) DOUBLE COMPARTMENT SKINCARE PRODUCTS COMPRISING AVERMECTIN/MILBEMYCIN COMPOUNDS

(75) Inventors: Sandrine Segura-Orsoni, Mandelieu (FR); Fabienne Louis, Villeneuve-loubet (FR)

(73) Assignee: Galderma S.A., Cham (CH)

( * ) Notice: Subject to any disclaimer, the term of this patent is extended or adjusted under 35 U.S.C. 154(b) by 672 days.

(21) Appl. No.: 12/385,521

(22) Filed: Apr. 10, 2009

(65) Prior Publication Data

US 2009/0286866 A1 Nov. 19, 2009

Related U.S. Application Data

(63) Continuation of application No. PCT/FR2007/052139, filed on Oct. 12, 2007.

(30) Foreign Application Priority Data

Oct. 12, 2006 (FR) ...................................... 06 54239

(51) Int. Cl.
*A61K 31/335* (2006.01)
*A61K 9/06* (2006.01)

(52) U.S. Cl.
CPC ........................................ *A61K 9/06* (2013.01)
USPC ........................................................ 514/450

(58) Field of Classification Search
None
See application file for complete search history.

(56) References Cited

U.S. PATENT DOCUMENTS

| 2003/0064940 A1 | 4/2003 | Parks |
| 2004/0167084 A1 | 8/2004 | Parks |
| 2006/0100165 A1 * | 5/2006 | Manetta et al. ................. 514/28 |

FOREIGN PATENT DOCUMENTS

| EP | 1 197 215 A2 | 4/2002 |
| EP | 1 668 984 A1 | 6/2003 |
| WO | WO 03/092583 A2 | 11/2003 |
| WO | WO 2004/093886 A1 | 11/2004 |

OTHER PUBLICATIONS

Database WPI Week 200634 "Powder Injection of Macrolides or N-Phenyl Pyrazole Deworming Drug" Thomas Scientific, 2006 XP002436631.
International Search Report PCT/FR2007/052139 dated Sep. 10, 2009.

* cited by examiner

*Primary Examiner* — Brian Gulledge
(74) *Attorney, Agent, or Firm* — Dentons US LLP

(57) ABSTRACT

Double compartment skincare products confine a first compartment containing an anhydrous composition including an active ingredient, and a second compartment, wherein the active ingredient is selected from among compounds of the avermectin family and compounds of the milbemycin family, and are useful as medicaments for the treatment and/or prevention of dermatological conditions/afflictions.

17 Claims, No Drawings

DOUBLE COMPARTMENT SKINCARE PRODUCTS COMPRISING AVERMECTIN/MILBEMYCIN COMPOUNDS

CROSS-REFERENCE TO EARLIER APPLICATIONS

This application is a continuation of PCT/FR 2007/052139, filed Oct. 12, 2007, and designating the United States (published in the French language on Apr. 17, 2008, as WO 2008/043974 A2; the title and abstract were also published in English), which claims priority under 35 U.S.C. §119 of FR 06/54239, filed Oct. 12, 2006, each hereby expressly incorporated by reference in its entirety and each assigned to the assignee hereof.

BACKGROUND OF THE INVENTION

1. Technical Field of the Invention

The present invention relates to skincare products containing a first anhydrous composition comprising at least one compound of the avermectin family or a compound of the milbemycin family, and a second composition, as a combination product for the treatment of dermatological conditions/afflictions.

2. Description of Background and/or Related and/or Prior Art

The avermectin and milbemycin families constitute a group of macrocyclic lactones produced by the bacterium *Streptomyces avermitilis* (Reynolds JEF (Ed) (1993) *Martindale. The extra pharmacopoeia,* 29th Edition, Pharmaceutical Press, London). Avermectins include in particular ivermectin, invermectin, avermectin, abamectin, doramectin, eprinomectin, emamectin and selamectin. Milbemycins include in particular lepimectin, milbemectin, milbemycin oxime, moxidectin and nemadectin.

Ivermectin, a compound of the avermectin family, is the preferred compound according to the present invention. Ivermectin is a mixture of two compounds belonging to the avermectin class, 5-O-demethyl-22,23-dihydroavermectin A1a and 5-O-demethyl-22,23-dihydroavermectin A1b. They are also known under the name 22,23-dihydroavermectin B1a and 22,23-dihydroavermectin B1b. Ivermectin contains at least 80% of 22,23-dihydroavermectin B1a and less than 20% of 22,23-dihydroavermectin B1b.

In the mid-1980s, ivermectin was presented as a broad-spectrum anti-parasitic medicament for veterinary use (CAMPBELL, W. C., et al., (1983). Ivermectin: a potent new anti-parasitic agent. Science, 221, 823-828). It is effective against most common intestinal worms (except taenias), most mites, and a few lice. It has in particular a high affinity for glutamate-gated chloride channels present in the nerve and muscle cells of invertebrates. Its attachment to these channels promotes an increase in membrane permeability to chloride ions, causing hyperpolarization of the nerve or muscle cell. This results in a neuromuscular paralysis which can cause the death of some parasites. Ivermectin also interacts with other ligand-gated chloride channels such as those involving the neuromediator GABA (gamma-aminobutyric acid). Ivermectin is more particularly an antihelminthic. It has already been described in humans in the treatment of *Onchocerca volvulus* onchocerciasis, gastrointestinal strongyloidiasis (anguillulosis) (product Stromectol®), human sarcoptic scabies (Meinking T L et al., *N. Engl. J. Med.,* 1995 Jul. 6; 333(1):26-30 The treatment of scabies with ivermectin) and in the treatment of diagnosed or suspected microfilaraemia in subjects suffering from lymphatic filariasis caused by *Wuchereria bancrofti.*

In addition, international application WO 2004/093886 discloses the use of ivermectin for the manufacture of a topical pharmaceutical composition intended for human use. More particularly, this application discloses the use of topical pharmaceutical compositions intended for human use comprising ivermectin for the treatment of dermatological conditions such as rosacea, acne vulgaris, seborrhoeic dermatitis, perioral dermatitis, acneform rash, transient acantholytic dermatitis and acne miliaris necrotica.

However, the low compatibility of ivermectin with many excipients (N. O, Shaw, M. M. de Villiers and A. P. Lötter, *Pharmazie,* 54 (1999) 5, 372-376 Preformulation stability screening of ivermectin with non-ionic emulsion excipients), and its low solubility in water mean that pharmaceutical compositions containing ivermectin generally require either the addition of a large number of additives which make it possible to obtain stable compositions, which has the effect of increasing the risk of allergies, or to be formulated with anhydrous excipients. The anhydrous compositions encountered conventionally have the disadvantage of a greasy feel and therefore of an appearance that is not very cosmetic, which may be responsible for a decrease in patient compliance. In addition, by virtue of the low stability of ivermectin in water, the shelf life of aqueous compositions containing ivermectin is generally shorter than that of anhydrous compositions containing ivermectin.

SUMMARY OF THE INVENTION

Considering the above, a problem which the invention proposes to solve is to make a stable skincare product, comprising an effective quantity of at least one compound of the avermectin family, or a compound of the milbemycin family, and more particularly comprising ivermectin, in suitable formulations which make it possible to avoid the degradation of the active agent in contact with water or in contact with raw materials capable of degrading it. Furthermore, the subject products increase patient compliance.

The solution given to this stated problem consists of a skincare product containing:

(a) a first, preferably pharmaceutical, anhydrous composition comprising, in a pharmaceutically acceptable medium, an active ingredient selected from among avermectins and milbemycins, preferably ivermectin, and (b) a second composition comprising pharmaceutically and/or cosmetically acceptable excipients, as a combination product useful for the treatment of dermatological conditions simultaneously, separately or spread out over time.

The expression "pharmaceutically acceptable medium" means a medium compatible with the skin, the mucous membranes and/or the superficial body growths.

DETAILED DESCRIPTION OF BEST MODE AND SPECIFIC/PREFERRED EMBODIMENTS OF THE INVENTION

Preferably, the present invention features a double compartment skincare product composed of a first compartment comprising the first anhydrous composition comprising an active ingredient, and a second compartment comprising the second composition, characterized in that said active ingredient is selected from among compounds of the avermectin family and compounds of the milbemycin family, and preferably ivermectin. The present invention therefore requires that the active ingredient in this anhydrous composition be soluble and stable. The anhydrous composition therefore preferably comprises simple constituents to limit any potentially disruptive interaction of the active ingredient with the said constituents. Consequently, as the emphasis is placed on the efficacy of the anhydrous composition of this first compartment, the second compartment contains a composition whose objective is advantageously to confer a pleasant appearance on the overall product for the patient. According to the invention, the second compartment contains an aqueous or anhydrous composition selected by one skilled in this art so as to confer the desired pleasant appearance on the product.

The expression "anhydrous composition" according to the invention means a composition comprising less than 5% of purified water by weight relative to the total weight of the composition.

The subject of the invention is also the use of the said product according to the invention for the manufacture of a medicament intended for the treatment of dermatological conditions.

Indeed, the skincare products, presented in a double compartment form, make it possible to limit as much as possible the interactions of the active agent selected from among avermectins and milbemycins, in particular ivermectin, with the numerous excipients usually contained in a single composition. The compositions according to the invention, applied simultaneously or successively, are thus very well tolerated, precise in terms of quantity of active agent delivered, and practical to use. They additionally offer comfort and moisturization to the patients.

The invention will be understood more clearly on reading the non-limiting description which follows.

The skincare products according to the invention are preferably composed of two compartments. This type of double compartment product, more commonly called "Dual Pack", already exists in the cosmetics field.

By way of non-limiting examples of dual pack models which can be used according to the invention, there may be mentioned the dual packs described in EP0644129, EP0243667 and U.S. Pat. No. 5,823,391. Among other currently marketed dual pack models which can be employed used according to the invention, there may be mentioned, and without limitation are:

the single outlet dual packs such as the model Duomixer™ marketed by Maplast™ or the model Symbio Dispenser™ marketed by Airspray™;

the double outlet dual packs such as the models new Duo Concept™, Duo Double Actuator™, Duo Normal™ marketed by Maplast™.

According to the invention, the skincare product comprises two compartments. The first compartment is composed of an anhydrous composition containing the active ingredient selected from among the avermectins and milbemycins, preferably ivermectin.

The ivermectin according to the invention contains at least 80% of 22,23-dihydroavermectin B1a and less than 20% of 22,23-dihydroavermectin B1b.

The composition of the first compartment according to the invention may be provided in the form of an anhydrous gel, an anhydrous emulsion or a simple anhydrous solution, that is to say, comprising a limited number, from two and six, of constituents.

The composition of the first compartment according to the invention preferably comprises from 0.001 to 50% of avermectin or milbemycin, preferably ivermectin, by weight relative to the total weight of the composition. More preferably, the composition of the first compartment comprises from 0.01 to 15% of avermectin or milbemycin, preferably ivermectin, by weight relative to the total weight of the composition.

According to the invention, the composition of the first compartment comprises avermectin or milbemycin, preferably ivermectin, in a form solubilized in a compound selected from among polar solvents, oils and amphiphilic solvents, and mixtures thereof.

By way of non-limiting examples of oily solvents in the compositions of the first compartment, there may be mentioned diisopropyl adipate marketed under the trademark Crodamol DA by Croda, PPG 15 stearyl ether marketed under the trademark Arlamol E by Uniqema, octyl dodecanol marketed under the trademark Eutanol G by Cognis, capric/caprylic triglycerides marketed under the trademark Miglyol 812 N by Sasol, alkyl benzoate marketed under the trademark Tegosoft TN by Croda.

By way of non-limiting examples of polar solvents which may be included in the compositions of the first compartment, there may be mentioned N-methylpyrrolidone marketed under the trademark Pharmasolve by ISP, dimethyl isosorbide marketed under the trademark Arlasolve DMI by Uniqema, phenoxyethanol marketed under the trademark Phenoxetol by Clariant, macrogol 15-hydroxystearate marketed under the trademark Solutol HS 15 by BASF, propylene glycol marketed by Merck, benzyl alcohol marketed by Merck, butyl alcohol, isopropanol and ethanol marketed in particular by Prolabo, macrogol 400 marketed under the trademark Lutrol 400 by BASF.

By way of non-limiting examples of amphiphilic solvents which may be included in the compositions of the first compartment, there may be mentioned polysorbate 80 marketed under the trademark Tween 80 V Pharma by Uniqema, poloxamer 124 marketed under the trademark Synperonic PE/L44 by Uniqema, oleyl alcohol marketed under the trademark HD-Eutanol V PH by Cognis, glycerol triacetate marketed under the trademark Triacétine by Lambert Riviere.

By way of non-limiting examples of lipophilic thickeners which may be included in the compositions of the first compartment, there may be mentioned glycerol distearate marketed under the trademark Precirol ATO and glycerol dibehenate marketed under the trademark Compritol 888 by Gattefossé, cetostearyl alcohol marketed under the trademark Speziol C18 by Cognis, colloidal silicon dioxide marketed under the trademark Aerosil 200 by Degussa.

By way of non-limiting examples of gelling agents which may be included in the compositions of the first compartment, there may be mentioned the acrylamide gel marketed under the trademark Simulgel 600 by SEPPIC, carbomers marketed under the trademarks Carbopol 980 NF and Carbopol 981 NF, acrylate/alkyl acrylate copolymers marketed under the trademark Pemulen TR1 and Pemulen TR2 marketed by Noveon, or glyceryl polymethacrylate and propylene glycol marketed under the trademark Lubragel CG by Guardian, polysaccharides, natural gums and clays.

According to a first advantageous embodiment, the composition of the first compartment is an anhydrous solution or gel comprising one or more polar solvents, which comprises at least:

0.1 to 99.99% of at least one polar solvent for the active agent;
0 to 5% of gelling agent(s);
0 to 10% of surfactant(s);
0.001 to 50% of active ingredient, preferably ivermectin;
0 to 3% of preservative(s).

According to a second advantageous embodiment, the composition of the first compartment is an anhydrous solution or gel comprising one or more oily solvents, which comprises at least:

0.1 to 99.89% of at least one oily solvent for the active agent;
 0.01 to 10% of active ingredient, preferably ivermectin;
 0.1 to 20% of gelling agent(s); and
 0 to 1% of preservative(s).

The composition of the second compartment is provided, according to the invention, in the form of a vehicle comprising cosmetically and/or pharmaceutically acceptable excipients, providing moisturization and comfort to the patient. The said composition may be aqueous or anhydrous and may be provided in the form of an emulsion, a gel, a solution or an unguent, preferably in the form of an emulsion or a gel. Such a composition thus comprises at least one moisturizing and/or emollient compound; these compounds may be selected in particular from among oils (for their emollient properties), or hydrophilic compounds, including water, present in the aqueous phase when it exists.

The cosmetically and/or pharmaceutically acceptable vehicle according to the invention should be selected such that the advantageous properties intrinsically attached to the present invention are not, or not substantially, impaired by the addition envisaged. The vehicle may be composed of a single excipient such as a solvent, or of a mixture of excipients such as those used for the formulation of an emulsion. By way of non-limiting examples of excipients which may be used alone or as a mixture, exemplary are water, solvents, diluents, any excipient which can be used for the formulation of an emulsion or a gel. These excipients are compounds commonly used in the formulation of pharmaceutical compositions. Preferably, the excipients according to the invention are water, alcohols, polyols, ethers, esters, aldehydes, ketones, fatty acids and alcohols, and fatty esters.

Advantageously, the compositions according to the invention are emulsions and may also comprise one or more surfactants in concentrations preferably ranging from 0.01 to 30%, and more preferably ranging from 0.1 to 6%.

In addition, the cosmetic and/or pharmaceutical compositions of the second compartment as described above may additionally comprise inert additives, or even pharmacodynamically active agents as regards pharmaceutical compositions, or combinations of these additives.

Of course, one skilled in this art will be careful to select the possible compound(s) to be added to these compositions and their respective quantities such that the advantageous properties intrinsically attached to the present invention are not, or not substantially, impaired by the addition envisaged.

Preferably, when the compositions of the second compartment are provided in anhydrous form, that is to say, comprising less than 5% of purified water by weight of the total weight of the composition, they are anhydrous emulsions or anhydrous gels.

According to a first advantageous embodiment, the composition of the second compartment is an anhydrous emulsion comprising at least:
 8 to 40% of oil;
 0.5 to 8% of emulsifier(s) having a hydrophilic-lipophilic balance (HLB) between 2 and 7;
 0 to 5% of coemulsifier(s) having an HLB greater than 6;
 0 to 8% of gelling agent(s);
 0 to 60% of humectant(s);
 0 to 5% of purified water; and
 0 to 3% of preservative(s).

According to a second advantageous embodiment, the composition of the second compartment is an anhydrous gel comprising at least:
 4 to 95% of silicone elastomer;
 2 to 20% of oil(s); and
 0 to 20% of thickener(s).

Preferably, when the compositions of the second compartment are provided in aqueous form, they are aqueous emulsions or aqueous gels.

According to a third advantageous embodiment, the composition of the second compartment is an aqueous emulsion of the oil-in-water (O/W) gel cream type, comprising at least:
 4 to 60% of oily phase;
 0.3 to 2% of polymeric emulsifier(s);
 0 to 2% of gelling agent(s);
 0 to 4% of coemulsifier(s);
 30 to 90% of purified water; and
 0 to 3% of preservative(s).

According to a fourth advantageous embodiment, the composition of the second compartment is an oil-in-water (O/W) aqueous emulsion, comprising at least:
 50 to 70% of aqueous phase;
 0 to 10% of emulsifier(s);
 0 to 4% of thickener(s);
 0.05 to 1% of gelling agent(s);
 0 to 20% of humectant(s); and
 0 to 3% of preservative(s).

According to a fifth advantageous embodiment, the composition of the second compartment is an aqueous gel, comprising at least:
 50 to 99.7% of purified water;
 0.3 to 2% of gelling agent(s);
 0 to 20% of humectant(s); and
 0 to 3% of preservative(s).

The compositions according to the invention are used as pharmaceutical products for human administration. More particularly, they are used for the treatment of dermatological conditions.

Thus, the invention also relates to the use of a double compartment skincare product comprising a first compartment composed of an anhydrous composition comprising at least one avermectin or milbemycin, preferably ivermectin, for the manufacture of a medicament intended for the treatment and/or prevention of dermatological conditions.

The expression "treatment and/or prevention of dermatological conditions" means, according to the present invention, the treatment and/or prevention of rosacea, acne vulgaris, seborrhoeic dermatitis, perioral dermatitis, acneform rash, transient acantholytic dermatitis and acne miliaris necrotica.

According to a preferred method of using the invention, the product is intended for the treatment of rosacea.

The present invention will now be illustrated by the following examples:

EXAMPLE 1

Study of the maximum solubility of ivermectin at T=1 hour at room temperature in various excipients.

| Excipients | Maximum solubility % (m/m) |
| --- | --- |
| N-Methyl-2-pyrrolidone | 58.13 |
| Dimethyl isosorbide | 35.20 |
| Propylene glycol (PG) | 21.83 |
| Phenoxyethanol | 15.70 |
| Ethanol rectapur | 14.47 |
| Macrogol 15 hydroxystearate | 10.60 |
| Diisopropyl adipate | 10.40 |
| Polysorbate 80 | 10.31 |

| Excipients | Maximum solubility % (m/m) |
|---|---|
| PEG 400 | 9.14 |
| Poloxamer 124 | 7.50 |
| Triacetin | 7.22 |
| Oleyl alcohol | 3.48 |
| PPG 15 stearyl ether | 3.30 |
| Octyl dodecanol | 2.50 |
| Capric/caprylic triglycerides | 1.70 |
| Alkyl benzoate | 1.60 |

The Table above presents a list of excipients whose maximum percentage solubility is greater than 1.60. These excipients represent the preferred solvents which may be used, alone or as a mixture, for the formulation of anhydrous simple compositions comprising the active ingredient ivermectin.

EXAMPLE 2

Comparative study of the chemical stability of ivermectin in various excipients.

| Excipients | Amount at T0 (%) | Storage at 25° C. for 1 month | Storage at 40° C. for 1 month |
|---|---|---|---|
| Diisopropyl adipate | 102.5 | 97.19 | 96.70 |
| Benzyl alcohol | 98.72 | 99.01 | 98.62 |
| PPG 15-stearyl ether | 102.48 | 98.61 | 98.07 |
| Phenoxyethanol | 99.42 | 97.77 | 98.56 |
| Macrogol 15-hydroxystearate | 98.76 | 95.32 | 71.88 |
| Poloxamer 124 | 98.09 | 98.19 | 92.34 |

The Table above therefore presents the differences in the solubility of ivermectin as a function of the excipients. A good stability of ivermectin in diisopropyl adipate, in benzyl alcohol, in PPG-15 stearyl ether and phenoxyethanol at room temperature or at 40° C. is noted in particular. On the other hand, ivermectin is less stable in macrogol 15-hydroxystearate and in poloxamer, in particular at the temperature of 40° C.

EXAMPLE 3

Skincare product comprising a first anhydrous compartment and a second aqueous compartment according to the invention, and its method of preparation.

Composition in the form of an anhydrous gel of the first compartment.

| INCI name | % formula | Phase |
|---|---|---|
| Propylene glycol | 89.40 | A |
| Ethanol rectapur | 5.00 | A |
| Benzyl alcohol | 3.00 | A |
| Ivermectin | 2.00 | A |
| Carbomer 980 NF | 0.30 | A |
| Triethanolamine | 0.30 | A |

Composition in the form of an oil-in-water emulsion of the second compartment.

| INCI name | % formula | Phase |
|---|---|---|
| Purified water | Qs 100% | A' |
| Methyl para-hydroxybenzoate | 0.25 | A' |
| Glycerol | 8.00 | A' |
| Disodium edetate | 0.10 | A' |
| Allantoin | 0.20 | A' |
| Carbomer 980 NF | 0.15 | A' |
| Acrylate/C10-30 alkyl acrylate crosspolymer | 0.30 | A' |
| Phenoxyethanol | 1.00 | A' |
| Propyl para-hydroxybenzoate | 0.10 | B |
| Paraffin oil | 10.00 | B |
| Sodium hydroxide (solution at 10%) | Qs pH 6.3 | C |

Procedure for the Composition of the First Compartment:

The formulation of the composition of the first compartment according to the invention is carried out under inactinic light. The various constituents of phase A (see above) are first weighed, and then the gelling agent is dispersed with rayneri stirring (deflocculating blade) until homogeneity is obtained. Finally, the composition is neutralized.

Procedure for the Composition of the Second Compartment:

The various constituents of phase B are first weighed and then heated to 65° C. The constituents of phase A' are also weighed, and then heated to 65° C. and then the polymeric emulsifier and the carbomer are dispersed until a homogeneous gel is obtained.

Phase B is then incorporated into phase A' with gentle rayneri stirring.

Finally, the mixture is neutralized at room temperature with phase C to obtain a pH of 6.3.

EXAMPLE 4

Skincare product comprising a first anhydrous compartment and a second aqueous compartment according to the invention, and its method of preparation.

Composition in the form of an anhydrous gel of the first compartment.

| INCI name | % formula | Phase |
|---|---|---|
| Diisodopropyl adipate | 89.50 | A |
| Glycerol dibehenate | 5.00 | A |
| Ivermectin | 2.00 | A |

Composition in the form of an oil-in-water emulsion of the second compartment.

| INCI name | % formula | Phase |
|---|---|---|
| Purified water | Qs 100% | A' |
| Methyl para-hydroxybenzoate | 0.15 | A' |
| Glycerol | 10 | A' |
| Disodium edetate | 0.1 | A' |
| Carbomer 980 NF | 0.3 | A' |
| Macrogol 2 stearyl ether | 2.5 | B |
| Macrogol 21 stearyl ether | 2.5 | B |
| PPG 15 stearyl ether | 8.00 | B |
| Propyl para-hydroxybenzoate | 0.05 | B |
| Sodium hydroxide (sol at 10%) | Qs pH 6.3 | C |

Procedure for the Composition of the First Compartment:

The formulation of the composition of the first compartment according to the invention is carried out under inactinic light. The various constituents of phase A are first weighed, and then the gelling agent is dispersed with rayneri stirring (deflocculating blade) until homogeneity is obtained.

Procedure for the Composition of the Second Compartment:

The various constituents of phase B are first weighed and then heated to 65° C. The constituents of phase A' are also weighed, and then heated to 65° C., and then the carbomer is dispersed until a homogeneous gel is obtained.

Phase B is then incorporated into phase A' with gentle rayneri stirring.

Finally, the mixture is neutralized at room temperature with phase C to obtain a pH of 6.3.

EXAMPLE 5

Skincare product comprising a first and a second anhydrous compartment according to the invention, and its method of preparation.

Composition in the form of an anhydrous solution of the first compartment.

| INCI name | % formula | Phase |
| --- | --- | --- |
| N-Methylpyrrolidone | 50.00 | A |
| Ethanol rectapur | 20.00 | A |
| Propylene glycol | 29.00 | A |
| Ivermectin | 1.00 | A |

Composition in the form of an anhydrous gel of the second compartment.

| INCI name | % formula | Phase |
| --- | --- | --- |
| Cyclomethicone/dimethicone crosspolymer | 92.00 | A' |
| Cyclopentasiloxane | 8.00 | A' |

Procedure for the Composition of the First Compartment:

The formulation of the composition of the first compartment according to the invention is carried out under inactinic light. The various constituents of phase A are first weighed, and then placed under rayneri stirring (deflocculating blade) until homogeneity is obtained.

Procedure for the Composition of the Second Compartment:

The various constituents of phase A' are first weighed, and then placed under rayneri stirring (deflocculating blade) until homogeneity is obtained.

EXAMPLE 6

Skincare product comprising a first anhydrous compartment and a second aqueous compartment according to the invention, and its method of preparation.

Composition in the form of an anhydrous solution of the first compartment.

| INCI name | % formula | Phase |
| --- | --- | --- |
| Macrogol 400 | 15.00 | A |
| Propylene glycol | 80.00 | A |
| Polysorbate 80 | 4.50 | A |
| Ivermectin | 0.50 | A |

Composition in the form of an aqueous gel of the second compartment.

| INCI name | % formula | Phase |
| --- | --- | --- |
| Purified water | Qs 100% | A' |
| Glycerol | 20.00 | A' |
| Disodium edetate | 0.1 | A' |
| Carbomer 980 NF | 0.50 | A' |
| Phenoxyethanol | 1.00 | A' |
| Sodium hydroxide (sol at 10%) | Qs pH 6.3 | B |

Procedure for the Composition of the First Compartment:

The formulation of the composition of the first compartment according to the invention is carried out under inactinic light. The various constituents of phase A are first weighed, and then placed under rayneri stirring (deflocculating blade) until homogeneity is obtained.

Procedure for the Composition of the Second Compartment:

The constituents of phase A' are first weighed, and then heated to 65° C., and then the carbomer is dispersed until a homogeneous gel is obtained.

The mixture is then neutralized at room temperature with phase B to obtain a pH of 6.3.

EXAMPLE 7

Skincare product comprising a first anhydrous compartment and a second aqueous compartment according to the invention, and its method of preparation.

Composition in the form of an anhydrous solution of the first compartment.

| INCI name | % formula | Phase |
| --- | --- | --- |
| PPG 15 stearyl ether | 80.00 | A |
| Octyldodecanol | 19.90 | A |
| Ivermectin | 0.10 | A |

Composition in the form of an aqueous gel of the second compartment.

| INCI name | % formula | Phase |
| --- | --- | --- |
| Purified water | Qs 100% | A' |
| Phenoxyethanol | 1.00 | A' |
| Sorbitol | 10.00 | A' |
| Disodium edetate | 0.10 | A' |
| Acrylamide/sodium acryloyldimethyl taurate copolymer & isohexadecane & polysorbate 80 | 1.00 | A' |

Procedure for the Composition of the First Compartment:

The formulation of the composition of the first compartment according to the invention is carried out under inactinic light. The various constituents of phase A are first weighed, and then placed under rayneri stirring (deflocculating blade) until homogeneity is obtained.

Procedure for the Composition of the Second Compartment:

The constituents of phase A' are first weighed, and then acrylamide/sodium acryloyidimethyl taurate copolymer & isohexadecane & polysorbate 80 is dispersed until a homogeneous gel is obtained.

EXAMPLE 8

Skincare product comprising a first anhydrous compartment and a second anhydrous compartment according to the invention, and its method of preparation.

Composition in the form of an anhydrous solution of the first compartment.

| INCI name | % formula | Phase |
|---|---|---|
| Propylene glycol | 98.50 | A |
| Hydroxyethylcellulose | 0.50 | A |
| Ivermectin | 1.00 | A |

Composition in the form of an anhydrous emulsion of the second compartment.

| INCI name | % formula | Phase |
|---|---|---|
| Lauryl methicone copolyol | 5.00 | A' |
| Cyclopentasiloxane | 10.00 | A' |
| Paraffin oil | 15.00 | A' |
| Glycerine | 40.00 | B |
| Glyceryl polymethacrylate (and) propylene glycol | 8.00 | B |
| Sorbitol | 17.00 | B |
| Purified water | 5.00 | B |

Procedure for the Composition of the First Compartment:

The formulation of the composition of the first compartment according to the invention is carried out under inactinic light. The various constituents of phase A are first weighed, and then placed under rayneri stirring (deflocculating blade) until homogeneity is obtained.

Procedure for the Composition of the Second Compartment:

The constituents of phase A' and B are first weighed, and then phase B is incorporated into phase A' with gentle rayneri stirring.

What is claimed is:

1. A single pack skincare product having two compartments:
   (a) a first compartment containing a first anhydrous composition comprising, in a pharmaceutically acceptable medium, an active ingredient which is ivermectin in a form which is solubilized in a member selected from the group consisting of polar solvents, oils, amphiphilic solvents and their mixtures, said first anhydrous composition being a solution or an anhydrous gel comprising at least, in percent by weight relative to the total weight of the composition:
      (i) from 0.1 to 99.99% of at least one polar solvent for the active ingredient;
      (ii) gelling agent(s) in an amount of up to 5%;
      (iii) from 0 to 10% of surfactant(s);
      (iv) from 0.001 to 50% of active ingredient; and
      (v) from 0 to 3% of preservative(s), and
   (b) a second compartment containing a second composition comprising pharmaceutically and/or cosmetically acceptable excipients and which comprise at least a moisturizing compound and/or emollient, as a combination product useful for the treatment of dermatological conditions/afflictions simultaneously, separately or spread out over time, wherein the first and second compartments are the only compartments in the skincare product, and wherein the single pack skincare product is to be marketed.

2. The skincare product as defined by claim 1, wherein the first anhydrous composition comprises from 0.01% to 15% by weight of ivermectin.

3. The skincare product as defined by claim 1, wherein the first anhydrous composition comprises an anhydrous gel or a simple anhydrous solution.

4. The skincare product as defined by claim 1, wherein the second composition is anhydrous.

5. The skincare product as defined by claim 1, wherein the second composition comprises an anhydrous emulsion.

6. The skincare product as defined by claim 5, wherein the second composition comprises an anhydrous emulsion including at least
   8 to 40% of oil;
   0.5 to 8% of emulsifier(s) having a hydrophilic-lipophilic balance (HLB) ranging between 2 and 7;
   0 to 5% of coemulsifier(s) having an HLB greater than 6;
   0 to 8% of gelling agent(s);
   0 to 60% of humectant(s);
   0 to 5% of purified water; and
   0 to 3% of preservative(s).

7. The skincare product as defined by claim 4, wherein the second composition comprises an anhydrous gel.

8. The skincare product as defined by claim 7, wherein the second composition comprises an anhydrous gel including at least:
   4 to 95% of silicone elastomer;
   2 to 20% of oil(s); and
   0 to 20% of thickener(s).

9. The skincare product as defined by claim 1, wherein the second composition is aqueous.

10. The skincare product as defined by claim 9, wherein the second composition comprises an aqueous emulsion.

11. The skincare product as defined by claim 10, wherein the second composition comprises a gel cream including at least:
    4 to 60% of oily phase;
    0.3 to 2% of polymeric emulsifier(s);
    0 to 2% of gelling agent(s);
    0 to 4% of coemulsifier(s);
    30 to 90% of purified water; and
    0 to 3% of preservative(s).

12. The skincare product as defined by claim 10, wherein the second composition comprises an oil-in-water emulsion including at least:
    50 to 70% of aqueous phase;
    0 to 10% of emulsifier(s);
    0 to 4% of thickener(s);
    0.05 to 1% of gelling agent(s);
    0 to 20% of humectant(s); and
    0 to 3% of preservative(s).

13. The skincare product as defined by claim 9, wherein the second composition comprises an aqueous gel.

14. The skincare product as defined by claim 13, wherein the second composition comprises an aqueous gel including at least:
    50 to 99.7% of purified water;
    0.3 to 2% of gelling agent(s);
    0 to 20% of humectant(s); and
    0 to 3% of preservative(s).

15. The skincare product as defined by claim 1, wherein the second composition comprises at least one active ingredient.

16. A method for the treatment of a dermatological condition or affliction selected from the group consisting of rosacea, acne vulgaris, seborrhoeic dermatitis, perioral dermatitis, acneform rash, transient acantholytic dermatitis and acne miliaris riecrotica, said method comprising topically applying to the skin of a subject in need of such treatment the skincare product as defined by claim 1.

17. The method as defined by claim 16, said dermatological condition/affliction being rosacea.

* * * * *